(12) United States Patent
Stahl et al.

(10) Patent No.: US 7,531,172 B2
(45) Date of Patent: May 12, 2009

(54) METHODS OF TREATING DISEASES WITH A VEGF ANTAGONIST

(75) Inventors: Neil Stahl, Carmel, NY (US); George D. Yancopoulos, Yorktown Heights, NY (US); Eric Furfine, New York, NY (US); Jesse M. Cedarbaum, Larchmont, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 124 days.

(21) Appl. No.: 11/502,736

(22) Filed: Aug. 11, 2006

(65) Prior Publication Data

US 2007/0037748 A1  Feb. 15, 2007

Related U.S. Application Data

(60) Provisional application No. 60/708,039, filed on Aug. 12, 2005.

(51) Int. Cl.
*A61K 38/18* (2006.01)
*C07K 14/71* (2006.01)
*C12N 15/62* (2006.01)

(52) U.S. Cl. ............... 424/134.1; 424/192.1; 514/2; 514/12; 530/350; 536/23.4

(58) Field of Classification Search ............. None
See application file for complete search history.

(56) References Cited

U.S. PATENT DOCUMENTS

| 6,100,071 | A | 8/2000 | Davis-Smyth et al. |
| 6,897,294 | B2 | 5/2005 | Davis-Smyth et al. |
| 2003/0144298 | A1 | 7/2003 | Curwen |
| 2005/0281831 | A1 | 12/2005 | Davis-Smyth et al. |

FOREIGN PATENT DOCUMENTS

| WO | WO 98/28006 | | 7/1998 |
| WO | WO 99/29861 | * | 6/1999 |
| WO | WO 2005/000895 | | 1/2005 |
| WO | WO 2005/123104 | | 12/2005 |

* cited by examiner

*Primary Examiner*—Christine J Saoud
*Assistant Examiner*—Jon M Lockard
(74) *Attorney, Agent, or Firm*—Valeta Gregg

(57) ABSTRACT

A method of reducing or preventing hypertension associated with administration of a vascular endothelial growth factor (VEGF) antagonist in a human subjects suffering from a disease or condition treatable with a VEGF antagonist in which is it desirable to reduce or prevent hypertension. The method is particularly useful for treatment of patients unresponsive to treatment with a VEGF inhibitor administered intravenously.

10 Claims, No Drawings

METHODS OF TREATING DISEASES WITH A VEGF ANTAGONIST

CROSS-REFERENCE TO RELATED APPLICATIONS

This application claims the benefit under 35 USC § 119(e) of U.S. Provisional 60/708,039 filed 12 Aug. 2005, which application is herein specifically incorporated by reference in its entirety.

BACKGROUND

1. Field of the Invention

The field of the invention is related to therapeutic methods of treating diseases in a human subject with a vascular endothelial growth factor (VEGF) antagonist such that side effects, such as an increase in blood pressure, are minimized. The patient population to be treated is a population in which it is desirable to minimize an increase in blood pressure.

2. Description of Related Art

Vascular endothelial growth factor (VEGF) has been recognized as a primary stimulus of angiogenesis in pathological conditions. Approaches to methods of blocking VEGF include soluble receptor constructs, antisense molecules, RNA aptamers, and antibodies. See, for example, PCT WO/0075319, for a description of VEGF-receptor based trap antagonists.

Hypertension has been reported at increased frequency and severity in subjects receiving the anti-VEGF humanized monoclonal antibody, bevacizumab (Hurwitz, et al, (2004) N. Engl. J. Med. 350:2335-42).

BRIEF SUMMARY OF THE INVENTION

In one aspect, the invention features a method of reducing hypertension associated with administration of a vascular endothelial cell growth factor (VEGF) antagonist, comprising administering the VEGF antagonist subcutaneously to a human subject in which it is desirable to minimize an increase in blood pressure.

More specifically, studies described below demonstrate that the increases in systolic and diasystolic blood pressure associated with intravenous administration of VEGF antagonists is largely eliminated by subcutaneous administration. The method of the invention is particularly useful for patients in which prevention of hypertension is desirable.

The method of the invention is useful with any VEGF antagonist which is associated with an increase in blood pressure when administered to a patient. In one embodiment, the VEGF antagonist is a high affinity fusion protein dimer (or "trap") comprising a fusion polypeptide having an immunoglobulin-like (Ig) domain 2 of the VEGF receptor Flt1 and Ig domain 3 of the VEGF receptor Flk1 or Flt4, and a multimerizing component. Even more specifically, the VEGF antagonist comprises a fusion polypeptide selected from the group consisting of Flt1D2.Flk1D3.FcΔC1(a) (SEQ ID NOs: 1-2), VEGFR1R2-FcΔC1(a) (SEQ ID NOs:3-4), or a functional equivalent thereof. Functionally equivalent molecules include dimeric proteins comprised of two fusion polypeptides which are expressed in a mammalian host cell and contain post-translational modification such as glycosylation, truncation of C-terminal lysine and/or signal peptide, etc.

In one aspect of the invention a "non-responder" patient is treated by subcutaneous administration of a vascular endothelial growth factor (VEGF) antagonist administered in a therapeutically effective amount and repeatedly administered over a therapeutically effective period of time. In accordance with the present invention the "non-responders" include individuals in need of treatment with a VEGF antagonist but when treated could not have sufficient amounts of the VEGF antagonist administered intravenously to be effective in that the administration of such caused and undesirable peak in the patient's blood pressure. Accordingly, such non-responders include those which initially suffer from high blood pressure which is not sufficiently controlled such that increasing that blood pressure would create a medical risk to the patient's health and further includes those patient's with normal blood pressure or blood pressure which is controlled within normal levels but when treated with a VEGF antagonist have their blood pressure rise to levels which create a medical risk to the patient.

Diseases and/or conditions, or recurrences thereof, which are ameliorated, inhibited, or reduced by treatment with a VEGF inhibitor are encompassed by the method of the invention. Such conditions include, for example, cancer, diabetes, vascular permeability, edema, or inflammation such as brain edema associated with injury, stroke, or tumor, edema associated with inflammatory disorders such as psoriasis or arthritis, asthma, edema associated with burns, ascites and pleural effusion associated with tumors, inflammation or trauma, chronic airway inflammation, capillary leak syndrome, sepsis kidney disease associated with increased leakage of protein, eye disorders such as age-related macular degeneration and diabetic retinopathy, abnormal angiogenesis such as polycystic ovary disease, endometriosis and endometrial carcinoma. A VEGF inhibitor may also be used to induce regression or reduction of the size of an existing tumor or metastatic cancer; diabetes, decrease tumor neovascularization, improve transplant corneal survival time, inhibit corneal transplant rejection or corneal lympangiogenesis and angiogenesis.

A subject to be treated is preferably a subject with one of the above-listed conditions who suffers from hypertension, is at risk for development of hypertension or in which the prevention or inhibition of hypertension is desirable, e.g., a subject at risk for cardiovascular disease, a subject over 65 years of age, or a patient who cannot otherwise be treated with an appropriate dose of the VEGF antagonist without developing hypertension.

In a second aspect, the invention features a method of preventing the development of hypertension during treatment with a vascular endothelial growth factor (VEGF) inhibitor in a patient at risk thereof, comprising administering a VEGF antagonist by subcutaneous injection to the patient.

Other objects and advantages will become apparent from a review of the ensuing detailed description.

DETAILED DESCRIPTION

Before the present methods and compositions are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

In the normal mammal, blood pressure is strictly controlled by a complex system of physiological factors. This is important for survival because high blood pressure (hypertension) can lead to a number of adverse medical events and conditions, such as, for example, stroke, acute coronary syndrome, myocardial infarction, and renal failure. Studies show that VEGF transiently dilates coronary arteries in vitro (Ku et. al. (1993) Am J Physiol 265:H585-H592) and induces hypotension (Yang et. al. (1996) J Cardiovasc Pharmacol 27:838-844). Methods for treating eclampsia and preemclampsia are known, for example, US patent application publication 2003/0220262, WO 98/28006, WO 00/13703, which describes a method for treating hypertension comprising administering to a patient an effective amount of an angiogenic factor such as VEGF, or an agonist thereof. US patent application publication 2003/0144298 shows that administration of high levels of a VEGF receptor tyrosine kinase inhibitor leads to a sustained increase in blood pressure in rats when administered chronically.

VEGF Antagonists and VEGF-Specific Fusion Polypeptide Traps

The method of the invention may be used with any VEGF antagonist which is associated with an increase in blood pressure when administered to a subject. In a preferred embodiment, the VEGF antagonist is a dimeric protein capable of binding VEGF with high affinity composed of two receptor-Fc fusion polypeptides consisting of the principal ligand-binding portions of the human VEGFRL and VEGFR2 receptor extracellular domains fused to the Fc portion of human IgG1 (the "VEGF trap"). Specifically, the VEGF "trap" consists of Ig domain 2 from VEGFR1, which is fused to Ig domain 3 from VEGFR2, which in turn is fused to the Fc domain of IgG1.

In a preferred embodiment, an expression plasmid encoding the VEGF trap is transfected into CHO cells, which secrete VEGF trap into the culture medium. The resulting VEGF trap is a dimeric glycoprotein with a protein molecular weight of 97 kDa and contains ~15% glycosylation to give a total molecular weight of 115 kDa. The fusion polypeptides forming the dimer are posttranslationally modified by glycosylation at one or more Asn residues and/or removal of the terminal Lys.

Since the VEGF trap binds its ligands using the binding domains of high-affinity receptors, it has a greater affinity for VEGF than do monoclonal antibodies. The VEGF trap binds VEGF-A ($K_D$=1.5 pM), PLGF1 ($K_D$=1.3 nM), and PLGF2 ($K_D$=50 pM); binding to other VEGF family members has not yet been fully characterized.

Treatment Population

A human subject preferably treated by the method described herein is a subject in which it is desirable to prevent or reduce one or more side effects resulting from treatment with an anti-angiogenic agent, such as hypertension, proteinuria. Particularly preferred subjects are those suffering from hypertension, over 65 years of age, or subjects in which reduction of or prevention of undesirable side effects allows an optimal therapeutic dose of the anti-angiogenic agent to be used which otherwise could not be used without placing the subject at risk for an adverse medical event. Patients suffering from renal cell carcinoma, pancreatic carcinoma, advanced breast cancer, colorectal cancer, malignant mesothelioma, multiple myeloma, ovarian cancer, or melanoma may be treated with the combined therapeutics of the invention. Diseases and/or conditions, or recurrences thereof, which are ameliorated, inhibited, or reduced by treatment with the combined therapeutics of the invention include cancer, diabetes, vascular permeability, edema, or inflammation such as brain edema associated with injury, stroke, or tumor, edema associated with inflammatory disorders such as psoriasis or arthritis, asthma, edema associated with burns, ascites and pleural effusion associated with tumors, inflammation or trauma, chronic airway inflammation, capillary leak syndrome, sepsis kidney disease associated with increased leakage of protein, eye disorders such as age-related macular degeneration and diabetic retinopathy, abnormal angiogenesis such as polycystic ovary disease, entometriosis and endometrial carcinoma. A VEGF inhibitor may also be used to induce regression or reduction of the size of an existing tumor or metastatic cancer; diabetes, decrease tumor neovascularization, improve transplant corneal survival time, inhibit corneal transplant rejection or corneal lymphangiogenesis and angiogenesis.

Combination Therapies

In numerous embodiments, a VEGF antagonist may be administered in combination with one or more additional compounds or therapies, including a second VEGF antagonist molecule and/or an antihypertensive agent. Combination therapy includes administration of a single pharmaceutical dosage formulation which contains a VEGF antagonist and one or more additional agents; as well as administration of a VEGF antagonist and one or more additional agent(s) in its own separate pharmaceutical dosage formulation. For example, a VEGF antagonist and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion protein of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

An "antihypertensive agent" when used herein refers to include calcium channel blockers, angiotensin converting enzyme inhibitors (ACE inhibitors), angiotensin II receptor antagonists (A-II antagonists), diuretics, β-adrenergic receptor blockers, vasodilators and α-adrenergic receptor blockers.

Calcium channel blockers include amlodipine; bepridil; clentiazem; diltiazem; fendiline; gallopamil; mibefradil; prenylamine; semotiadil; terodiline; verapamil; aranidipine; barnidipine; benidipine; cilnidipine; efonidipine; elgodipine; felodipine; isradipine; lacidipine; lercanidipine; manidipine; nicardipine; nifedipine; nilvadipine; nimodipine; nisoldipine; nitrendipine; cinnarizine; flunarizine; lidoflazine; lomerizine; bencyclane; etafenone; and perhexyline.

Angiotensin converting enzyme inhibitors (ACE-Inhibitors) include alacepril; benazepril; captopril; ceronapril; delapril; enalapril; fosinopril; imidapril; lisinopril; moveltipril; perindopril; quinapril; ramipril; spirapril; temocapril; and trandolapril.

Angiotensin-II receptor antagonists include, but are not limited to: candesartan (U.S. Pat. No. 5,196,444); eprosartan; irbesartan; losartan; and valsartan.

β-blockers include, but are not limited to: acebutolol; alprenolol; amosulalol; arotinolol; atenolol; befunolol; betaxolol; bevantolot; bisoprolol; bopindolol; bucumolol; bufetolol; bufuralol; bunitrolol; bupranolol; butidrine hydrochloride; butofilolol; carazolol; carteolol; carvedilol; celiprolol; cetamolol; cloranololdilevalol; epanolol; indenolol; labetalol; levobunolol; mepindolol; metipranolol; metoprolol; moprolol; nadolol; nadoxolol; nebivalol; nipradilol; oxprenolol; penbutolol; pindolol; practolol; pronethalol; propranolol; sotalol; sulfinalol; talinolol; tertatolol; tilisolol; timolol; toliprolol; and xibenolol.

α-blockers include, but are not limited to: amosulalol; arotinolol; dapiprazole; doxazosin; fenspiride; indoramin; labetolol, naftopidil; nicergoline; prazosin; tamsulosin; tolazoline; trimazosin; and yohimbine.

Vasodilators include cerebral vasodilators, coronary vasodilators and peripheral vasodilators. Cerebral vasodilators include bencyclane; cinnarizine; citicoline; cyclandelate; ciclonicate; diisopropylamine dichloroacetate; eburnamonine; fasudil; fenoxedil; flunarizine; ibudilast; ifenprodil; lomerizine; nafronyl; nicametate; nicergoline; nimodipine; papaverine; tinofedrine; vincamine; vinpocetine; and viquidil.

Coronary vasodilators include, but are not limited to: amotriphene; bendazol; benfurodil hemisuccinate; benziodarone; chloracizine; chromonar; clobenfural; clonitrate; cloricromen; dilazep; dipyridamole; droprenilamine; efloxate; erythrityl tetranitrate; etafenone; fendiline; floredil; ganglefene; hexestrol bis(β-diethylaminoethyl)ether; hexobendine; itramin tosylate; khellin; lidoflazine; mannitol hexanitrate; medibazine; nitroglycerin; pentaerythritol tetranitrate; pentrinitrol; perhexyline; pimefylline; prenylamine; propatyl nitrate; trapidil; tricromyl; trimetazidine; troInitrate phosphate; visnadine.

Peripheral vasodilators include, but are not limited to: aluminium nicotinate; bamethan; bencyclane; betahistine; bradykinin; brovincamine; bufeniode; buflomedil; butalamine; cetiedil; ciclonicate; cinepazide; cinnarizine; cyclandelate; diisopropylamine dichloroacetate; eledoisin; fenoxedil; flunarizine; hepronicate; ifenprodil; iloprost; inositol niacinate; isoxsuprine; kallidin; kallikrein; moxisylyte; nafronyl; nicametate; nicergoline; nicofuranose; nylidrin; pentifylline; pentoxifylline; piribedil; prostaglandin $E_1$; suloctidil; tolazoline; and xanthinol niacinate.

Diuretics include but are not limited to diuretic benzothiadiazine derivatives, diuretic organomercurials, diuretic purines, diuretic steroids, diuretic sulfonamide derivatives, diuretic uracils and other diuretics such as amanozine; amiloride; arbutin; chlorazanil; ethacrynic acid; etozolin;

hydracarbazine; isosorbide; mannitol; metochalcone; muzolimine; perhexyline; ticrynafen; triamterene; and urea.

Methods of Administration

The invention provides compositions and methods of treatment with a VEGF antagonist which avoids, reduces, or eliminates an increase in blood pressure associated with VEGF antagonist administration. Accordingly, in the method of the invention, the VEGF antagonist is administered subcutaneously to the subject in need of such treatment.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and mucoadhesive.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Subcutaneous Administration of a VEGF Antagonist

Study 0103. An initial cohort of 3 patients were dosed subcutaneously with 25 ug/kg with the receptor-based VEGF antagonist ("VEGF trap") (SEQ ID NO:4) with a series of six weekly injections. Four weeks later, 3 additional patients were enrolled in the cohort and received six weekly injections of 50 ug/kg. Four weeks later, 3 additional patients were enrolled in the cohort and received six weekly injections of 50 ug/kg. This schedule was repeated, enrolling 3 patients in each cohort dose group of 100 ug/kg, 200 ug/kg, 400 ug/kg and 800 ug/kg. An additional cohort was added and received 800 ug/kg twice per week.

Patients were required to meet the following criteria for enrollment: (1) patients with relapsed or refractory solid tumor (other than squamous cell carcinoma of the lung), or non-Hodgkin's lymphoma refractory to at least two standard chemotherapy regimens and rituximab, and at least one measurable site of metastases or residual primary tumor; (2) No history of CNS primary tumor or metastasis; (3) Patients who have failed all curative chemotherapeutic regimens for their underlying disease and who have no standard chemotherapy, immunotherapy, anti-tumor therapy or radiotherapy options available; (4) Adequate organ function; (5) Acceptable laboratory parameters, including coagulation profile and renal function tests.

Both supine and standing blood pressure were monitored at each study visit in the Protocol. In cases of new hypertension or worsening of previously documented hypertension, blood pressure was readily managed with 1 or 2 antihypertensive agents.

Exploratory analyses of blood pressure dose-resDonse. The dose level cohorts were combined into 4 dose groups to facilitate the use of statistical tools to examine potential trends. Combined dose group 1 includes subjects treated at the 25 µg/kg, 50 µg/kg, and 100 µg/kg dose levels; combined dose group 2 includes subjects treated at the 200 µg/kg and 400 µg/kg; dose levels; combined dose group 3 includes subjects treated at the 800 µg/kg; and combined dose group 4 includes subjects treated at the 800 µg/kg twice weekly dose level. Using these combined dose groups, group differences at each time point were assessed using analysis of variance (ANOVA) as a descriptive tool to flag potential trends. Simple linear regression analysis was also applied to test the linear trend. Separate analyses were undertaken for supine and standing, systolic and diastolic blood pressures.

Standing systolic blood pressure. For change in standing systolic blood pressure, the ANOVA at each time point revealed no dose-related trend toward an increase in standing systolic blood pressure; only the Day 3 out of 14 time assessments appeared to have a nominal p-value less than 0.05. Mean change from baseline determinations obtained in the first 2 weeks of administration are shown in Table 1.

Standing diastolic blood pressure. For change in standing diastolic blood pressure, the ANOVA on mean values at each time point again revealed no dose-related trend. None of the 14 time assessments had nominal p-value less than 0.05, but 4 of the time assessments time had nominal p-values between 0.05 and 0.1. Mean change from baseline determinations obtained in the first 2 weeks of administration are shown in Table 1.

Example 2

Intravenous Administration of a VEGF Antagonist

Study 0202. Patients with refractory solid tumors or non-Hodgkin's lymphoma receiving no concurrent treatment for their cancer are treated with the VEGF trap (SEQ ID NO:4) as follows. An initial cohort of 3 patients received a single dose of 0.3 mg/kg VEGF trap administered intravenously. As the single dose was well tolerated, patients received one additional infusion at the same dose level after a 2-week interval. An additional cohort of 3 patients received 1.0 mg/kg VEGF trap intravenously following the same schedule. This pattern was repeated with dose level cohorts of 3-6 patients receiving 2.0, 3.0, and 4.0 mg/kg VEGF trap. Blood pressure is monitored and tumor burden is assessed at the beginning and end of the weekly dosing period; patients with stable disease, partial or complete responses may continue dosing for up to an additional 6 months in a continuation study. Mean changes at Day 15 from baseline Day 0 are shown for each dose group in Table 1.

Study 0305. A second study was conducted following the procedure for study 0202. Patients selected for the study had relapsed or refractory solid tumors (other than squamous cell carcinoma of the lung) who were not expected to benefit from standard therapy, or non-Hodgkin's lymphoma refractory to at least two standard chemotherapy regimens and rituximab, and at least one measurable site of metastasis or residual primary tumor, and had completed Study 0202 without experience dose-limiting toxicity.

Systolic and diastolic blood pressure measurements were obtained as described in Example 1. Mean change from baseline determinations obtained in the first 2 weeks of administration are shown in Table 1 for each study group.

Generally, subcutaneous administration of the VEGF trap resulted in an increased blood pressure of 3.8-8.2% at the highest dose level. Intravenous administration resulted in an increase in blood pressure of over 20% at the highest doses. At comparable doses, a subcutaneously administered dose of 800 ug/kg VEGF trap resulted in a 1.5% increase in diastolic blood pressure, whereas an intravenous dose of 1.0 mg/kg VEGF trap increased diastolic blood pressure 3.7-13.3%.

TABLE 1

Summary of Results for Subcutaneous (0103) and Intravenous (0202, 0305) Studies

| Study | Dose | | | |
|---|---|---|---|---|
| 0103 | 25, 50, 100 µg/kg | 200-400 µg/kg | 800 µg/kg | 1600 µg/kg |
| Systolic | −1.92 | −0.75 | −1.17 | 8.17 |
| Diastolic | −2.42 | −2.83 | 1.5 | 3.83 |
| 0202 | 0.3 mg/kg | 1.0 mg/kg | 2.0 mg/kg | 3.0 mg/kg | 4.0 mg/kg |
| Systolic | 1.0 | 0 | 1.2 | 17 | −0.5 |
| Diastolic | 1.0 | 3.17 | 0.4 | 5 | 3.5 |
| 0305 | 0.0 | 0.3 mg/kg | 1.0 mg/kg | 3.0 mg/kg |
| Systolic | −3.8 | 3 | 8.0 | 22.8 |
| Diastolic | 3.3 | 11.0 | 13.3 | 20.4 |

The present invention may be embodied in other specific forms without departing from the spirit or essential attributes thereof.

What is claimed is:

1. A method of treating a condition which is ameliorated, reduced or inhibited with a vascular endothelial growth factor (VEGF) antagonist in a patient in whom it is desirable to minimize an increase in blood pressure associated with administration of a VEGF antagonist, comprising:
   (a) identifying a patient who exhibits an abnormally high blood pressure level when administered a VEGF antagonist intravenously, wherein the abnormally high blood pressure level associated with intravenously administered VEGF antagonist is considered to raise an unacceptable medical risk to the patient; and
   (b) subcutaneously administering to the patient a therapeutically effective amount of the VEGF antagonist such that the condition is ameliorated, reduced or inhibited, wherein the increased blood pressure associated with administration of a VEGF antagonist is minimized.

2. The method of claim 1, further comprising:
   (c) monitoring the patient's blood pressure during and after the subcutaneous administration of the VEGF antagonist.

3. The method of claim 2, further comprising:
   (d) repeatedly administering the VEGF antagonist by subcutaneous administration.

4. The method of claim 1, wherein the VEGF antagonist is VEGFR1R2-FcΔC1(a) (SEQ ID NO:4).

5. The method of claim 4, further comprising administering at least one anti-hypertensive agent.

6. The method of claim 5, wherein the at least one anti-hypertensive agent is administered simultaneously or sequentially with respect to the VEGF antagonist.

7. The method of claim 1, wherein the identified patient suffers from hypertension.

8. The method of claim 1, wherein the patient has a blood pressure reading within normal ranges which patient blood pressure increases to an unacceptable risk level after administration of the VEGF antagonist by intravenous administration.

9. A method of treating a human subject suffering from a condition which is ameliorated, reduced or inhibited by administration of a vascular endothelial growth factor (VEGF) antagonist, wherein it is desirable to minimize an increase in blood pressure associated with intravenous administration of a VEGF antagonist, comprising:
   (a) identifying a patient in whom it is desirable to minimize an increase in blood pressure;
   (b) administering to the patient a therapeutically effective amount of a VEGF antagonist by subcutaneous administration, wherein the VEGF antagonist is VEGFR1R2-FcΔC1 (a) (SEQ ID NO:4) and the increase in blood pressure associated with administration of a VEGF antagonist is reduced or inhibited;
   (c) monitoring the patient's blood pressure during and after the subcutaneous administration of the VEGF antagonist; and
   (d) repeatedly administering the VEGF antagonist by subcutaneous administration.

10. The method of claim 9, further comprising administering at least one anti-hypertensive agent.

* * * * *

SEQUENCE LISTING

<160> NUMBER OF SEQ ID NOS: 4

<210> SEQ ID NO 1
<211> LENGTH: 1453
<212> TYPE: DNA
<213> ORGANISM: Artificial Sequence
<220> FEATURE:
<223> OTHER INFORMATION: Synthetic

<400> SEQUENCE: 1

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gaccttttcgt agagatgtac agtgaaatcc     180
ccgaaattat acacatgact gaaggaaggg agctcgtcat tcctgccgg gttacgtcac     240 ctaacatcac tgttactttta aaaaagtttc cacttgacac tttgatccct gatggaaaac     300
gcataatctg ggacagtaga aagggcttca tcatatcaaa tgcaacgtac aaagaaatag     360
ggcttctgac ctgtgaagca acagtcaatg ggcatttgta taagacaaac tatctcacac     420
atcgacaaac caatacaatc atagatgtgg ttctgagtcc gtctcatgga attgaactat     480
ctgttggaga aaagcttgtc ttaaattgta cagcaagaac tgaactaaat gtgggggattg     540 acttcaactg ggaataccct tcttcgaagc atcagcataa gaaacttgta aaccgagacc     600
taaaaaccca gtctgggagt gagatgaaga aatttttgag caccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc ccccaaaac     840 ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
```

```
ccctcccagc ccccatcgag aaaaccatct ccaaagccaa agggcagccc cgagaaccac      1140
aggtgtacac cctgccccca tcccgggatg agctgaccaa gaaccaggtc agcctgacct      1200
gcctggtcaa aggcttctat cccagcgaca tcgccgtgga gtgggagagc aatgggcagc      1260
cggagaacaa ctacaagacc acgcctcccg tgctggactc cgacggctcc ttcttcctct      1320
atagcaagct caccgtggac aagagcaggt ggcagcaggg gaacgtcttc tcatgctccg      1380
tgatgcatga ggctctgcac aaccactaca cgcagaagag cctctccctg tctccgggta      1440
aatgagcggc cgc                                                        1453
```

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
```

```
            290                 295                 300
Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
    450                 455

<210> SEQ ID NO 3
<211> LENGTH: 1377
<212> TYPE: DNA
<213> ORGANISM: Artificial Sequence
<220> FEATURE:
<223> OTHER INFORMATION: Synthetic

<400> SEQUENCE: 3
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaacttgt aaaccgagac     540 ctaaaaaccc agtctgggag tgagatgaag aaattttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta acagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aagggcagc ccgagaacc acaggtgtac    1080 accctgcccc catcccggga tgagctgacc aagaaccagg tcagcctgac ctgcctggtc    1140
```

```
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

<210> SEQ ID NO 4
<211> LENGTH: 458
<212> TYPE: PRT
<213> ORGANISM: Artificial Sequence
<220> FEATURE:
<223> OTHER INFORMATION: Synthetic

<400> SEQUENCE: 4

```
Met Val Ser Tyr Trp Asp Thr Gly Val Leu Leu Cys Ala Leu Leu Ser
 1               5                  10                  15

Cys Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320
```

```
-continued

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```